United States Patent [19]

Drewlow

[11] Patent Number: Plant 6,306

[45] Date of Patent: Sep. 27, 1988

[54] IMPATIENS PLANT NAMED SUNGLOW

[75] Inventor: Lyndon W. Drewlow, Ashtabula, Ohio

[73] Assignee: Mikkelsens, Inc., Ashtabula, Ohio

[21] Appl. No.: 916,565

[22] Filed: Oct. 8, 1986

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Evans

[57] ABSTRACT

An Impatiens plant named Sunglow, having orange and cream-white bicolor flower petals; small leaves having a heavy cream center variegation; two flowers per leaf axil resulting in a floriferous habit; and having a vigorous, self-branched and dense compact growth habit.

2 Drawing Sheets

The present invention relates to a new and distinctive cultivar of Impatiens plant, botanically known as Impatiens, and referred to by the cultivar name Sunglow. Sunglow was developed by me through controlled breeding by crossing Mikkelsen Seedling No. 82-873-1 (seed parent) with Mikkelsen Seedling No. 83-513-3 (pollen parent). Asexual reproduction of the progeny of the stated cross by terminal or stem cuttings performed in Ashtabula, Ohio has shown that unique features of this new Impatiens are stabilized and are reproduced true to type in successive propagations.

The following characteristics in combination distinguish the new Impatiens from both its parent varieties and other cultivated Impatiens of this type known and used in the floriculture industry. In certain instances the characteristics of Sunglow are compared with similar characteristics of other cultivars. Of the cultivars referred to, Astro is disclosed in U.S. Plant Pat. No. 4,691, and Sunregal, Sunburst, Sundazzle and Twilight are disclosed in pending applications.

1. Sunglow has a distinct medium orange and cream-white bicolor flower which is similar in pattern to Sunregal, Sundazzle, and Sunburst. Twilight is only slightly bicolored, and Astro is only bicolored on the upper petal.

2. Sunglow has a medium red main stem which is similar to Astro and Sunburst. Sunregal and Twilight have more red pigment in their stems, while Sundazzle only has a touch of red in its stem.

3. Flower size of Sunglow is smaller than Astro, Twilight, Sundazzle, Sunregal and Sunburst.

4. Sunglow is larger than Sundazzle and Sunburst in plant size but has a similar mounded habit. Sunglow is similar in size to Sunregal but more mounded, and is more compact and dense than either Astro or Twilight.

5. Sunglow has heavy cream center variegation of the leaves which is similar to Astro and Twilight. Sunregal and Sundazzle have no variegation, and Sunburst has only a small amount of variegation of the midrib near the bottom of the leaf on mature foliage.

6. Sunglow has small leaves, being similar to Sunregal in leaf size. Astro, Twilight, Sundazzle and Sunburst all have larger leaves.

7. The main leaf color of Sunglow is a dull dark green which is similar to Twilight. Astro has more purple in the green, Sunregal has a shiny dark green leaf, and Sundazzle and Sunburst have a more yellow green leaf.

8. Sunglow has two flowers per leaf axil which is similar to Sundazzle, Sunregal and Sunburst, while Astro and Twilight only have one flower per leaf axil.

9. Sunglow is highly self-branched, vigorous, dense and small-leaved making it suitable for 4" pots, hanging baskets and bedding plant use.

10. Flowering is 3 to 5 days earlier than Twilight and Astro, but 3 to 5 days later than Sunregal, Sundazzle and Sunburst under greenhouse conditions in the spring.

Of the accompanying colored photographs, sheet 1 is a perspective view showing the overall appearance of Sunglow, showing the colors as true as it is reasonably possible to obtain in a colored reproduction of this type.

Sheet 2 is a color photograph showing the bicolor flower color of Sunglow in enlarged form.

The following is a detailed description of Sunglow based on plants produced under commercial practices in Ashtabula, Ohio under both greenhouse and outdoor conditions. Photographs were taken on greenhouse grown plants in early June. Color references are made to The Royal Horticultural Society Colour Chart except where general terms of ordinary dictionary significance are used.

Parentage: A controlled cross between Mikkelsen Seedling No. 82-873-1 and Mikkelsen Seedling No. 83-513-3.

Propagation:

(A) *Type cutting.*—Stem 15 mm long will develop to 4 to 5 cm long in 18 to 21 days.

(B) *Time to root.*—8 to 10 days at 23° C. summer, and 10 to 12 days at 20° C. winter.

(C) *Rooting habit.*—Heavy, fibrous.

Plant description:

(A) *Form.*—Compact, symmetrically mounded, light red stemmed, vigorous flowering herb.

(B) *Habit of growth.*—Vigorous, dense, compact, self-branched, mounded, continuous flowering with flowers over the top of the foliage.

(C) *Foliage description.*—Small dark green leaves with golden yellow variegation in the center of the leaf going almost to the tip on mature plants. (1) Size: 7 to 8 cm long by 1.5 to 2.0 cm wide at the widest point. (2) Shape: Lanceolate with acuminate apex and acute base. (3) Texture: Upper side slightly rugose and underside glabrous. (4) Margin: Entire with fine cilia. (5)

Color: Young foliage top side 146A. Under side: 138A. Mature foliage top side 147A, variegated with 163A. Under side: 183 B, variegated with 180A. (6) Venation: Pinnate; midrib is reddish in color.

Flowering description:

(A) *Flowering habits.*—Flowers continuously from leaf whorl in progressively orderly manner taking 5 to 7 days from large bud to bloom. Each leaf axil has two flowers. All primary flowers open in a whorl before the secondary flowers begin to open, beginning with the same axil that opened the first primary flower. When the secondary flowers are about finished opening, the primary flowers of the whorl above start to open. Flowers last 2 to 3 weeks.

(B) *Natural flowering season.*—Indeterminant and continuous. Quantity of flowering increases with increasing levels of light.

(C) *Flower buds.*—Ellipsoidal, flowers perfect, reddish spur approximately 3 cm long on mature buds with throat behind ovary and originating from the major sepal.

(D) *Flowers borne.*—On individual 4.0 to 4.5 cm pedicels from a whorl of 5 leaves, flowering progressively around the whorl as leaves and buds develop. All primary flowers in a whorl flower before the secondary ones start. Flowers both over and in the leaf canopy.

(E) *Quantity of flowers.*—Floriferous due to the two flowers per leaf axial. Flowering development is continuous so that tight buds to mature bloom are visible at the same time.

(F) *Petals.*—(1) Shape: Heart shaped, top petal dominant over other petals; 4 overlapping and symmetrical. (2) Color: Top side in summer when opening, dull 34A and 49B, fading to 34A and 49C and D; under side 34B. (3) Number of petals: Five (5) in number. (4) Size of flowers: 3.5 to 4.0 cm in diameter.

(G) *Reproductive organs.*—(1) Stamens: Five (5) in number. (a) Anther shape: Hooded, color cream. (b) Pollen color: Cream. (2) Pistels (a) Stigma: Five (5) in number, segmented, column shaped, color purplish. (b) Style color: Purplish. (c) Ovaries: Five (5) in number, celled, size 4 mm until fertilized, purplish in color with hint of green.

Disease resistance: No significant disease or insect problems noted to date.

SUMMARY OF IMPORTANT CHARACTERISTICS OF NEW CULTIVAR

1. Small leaves and dense compact plant make Sunglow excellent for 10 and 14 cm pots.

2. Performs very well under low light and 70° F. conditions, continuing to flower without loss of flower size or fading or severe leaf drop.

I claim:

1. A new and distinct Impatiens plant named Sunglow, as described and illustrated, and particularly characterized by its orange and cream-white bicolor flower petals; small leaves having a heavy cream center variegation; two flowers per leaf axil resulting in a floriferous habit; and by its vigorous, self-branched and dense compact growth habit.

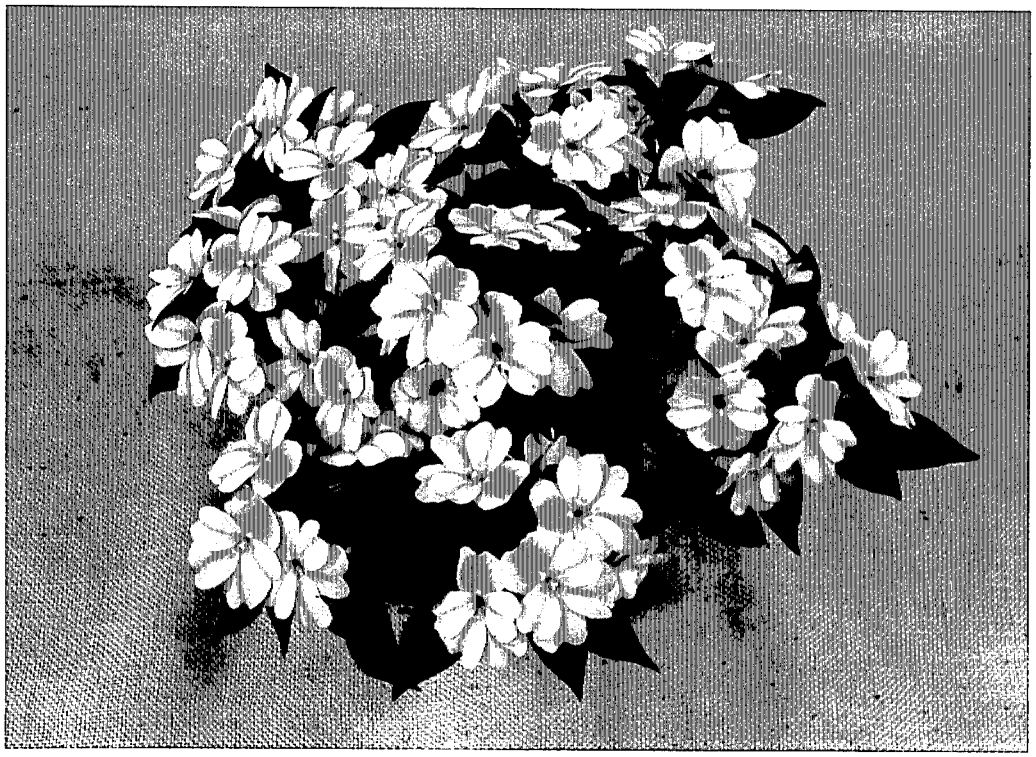

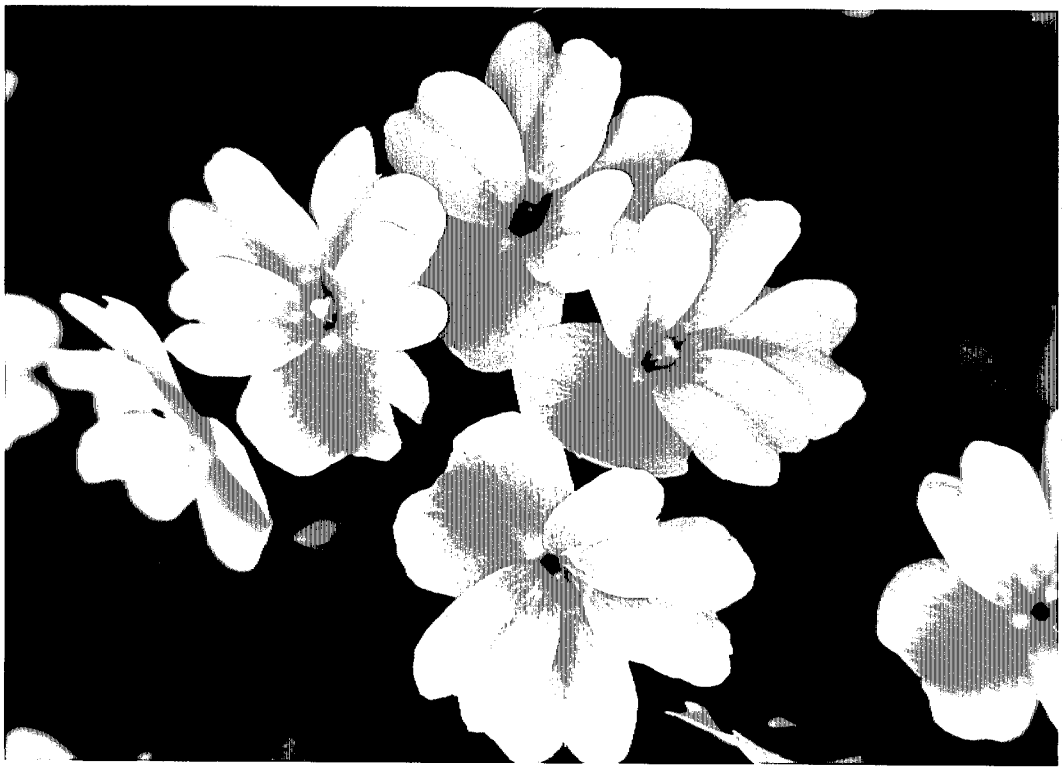

* * * * *